United States Patent [19]
Harding

[11] Patent Number: 5,986,257
[45] Date of Patent: Nov. 16, 1999

[54] METHOD OF DETECTING AN OBJECT IN AN EXAMINATION ZONE, AND DEVICE FOR CARRYING OUT THE METHOD

[75] Inventor: Geoffrey Harding, Hamburg, Germany

[73] Assignee: U.S. Philips Corporation, New York, N.Y.

[21] Appl. No.: 08/868,230

[22] Filed: Jun. 3, 1997

[30] Foreign Application Priority Data

Jun. 7, 1996 [DE] Germany .......................... 196 22 758

[51] Int. Cl.⁶ .................................................. G01N 23/203
[52] U.S. Cl. .............................................. 250/253; 378/88
[58] Field of Search ................................ 250/253; 378/88

[56] References Cited

U.S. PATENT DOCUMENTS 5,115,459  5/1992  Bertozzi ..................................... 378/88
5,729,582  3/1998  Ham et al. ................................. 378/89

FOREIGN PATENT DOCUMENTS

0358237B1  3/1990  European Pat. Off. .
3047824C2  10/1981  Germany .

*Primary Examiner*—Constantine Hannaher
*Attorney, Agent, or Firm*—Anne E. Barschall

[57] ABSTRACT

A method of detecting an object in an examination zone is well-suited for detecting land mines buried in the soil. The mean atomic numbers of the object is different from that of the examination zone. The examination zone is irradiated by gamma radiation. The annihilation radiation thus generated is measured and evaluated. The gamma radiation, which is sufficiently strong to generate electron-positron pairs, amounts to less than 10 MeV. The radiation generated in the examination zone by the gamma radiation beam is detected by a plurality of detector elements, which are arranged in such a manner that they can always detect only a respective segment of the gamma radiation beam.

12 Claims, 1 Drawing Sheet

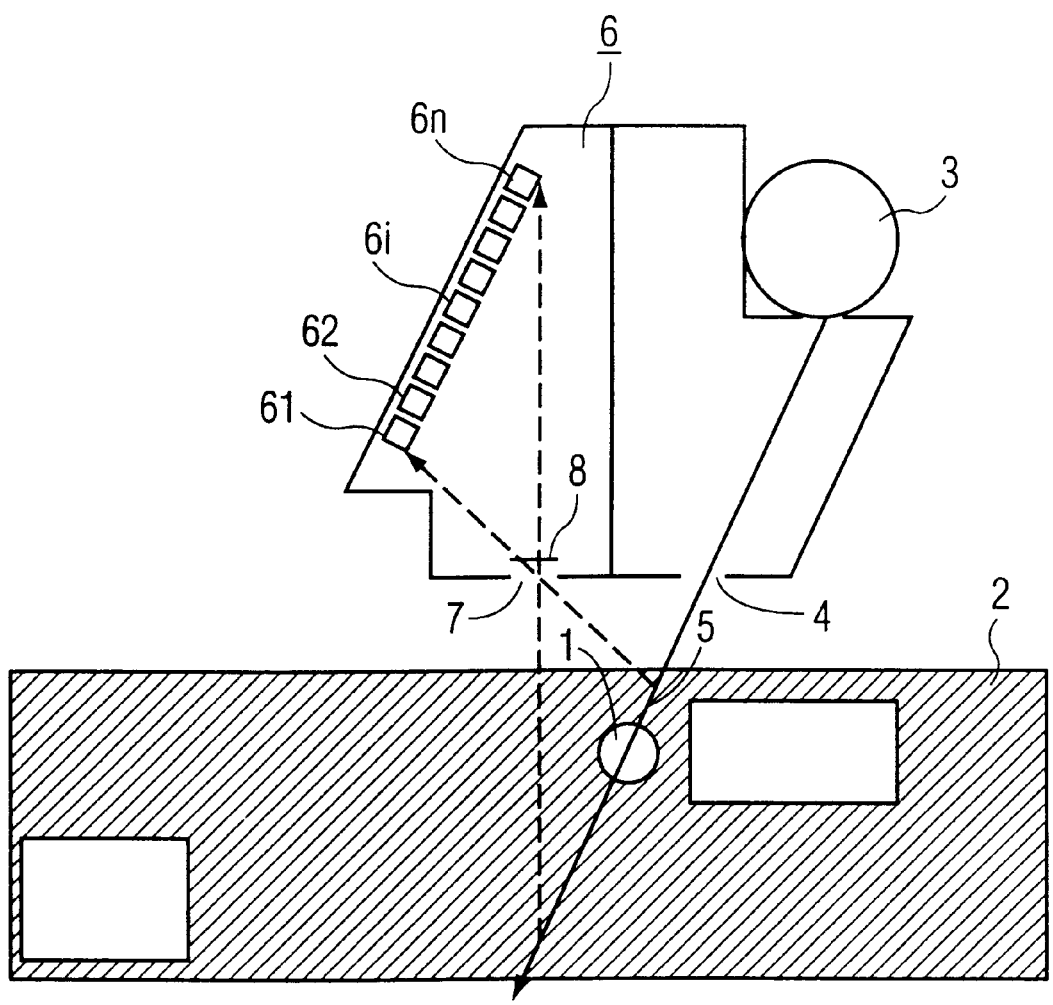

METHOD OF DETECTING AN OBJECT IN AN EXAMINATION ZONE, AND DEVICE FOR CARRYING OUT THE METHOD

The invention relates to a method of detecting an object in an examination zone, the mean atomic numbers of the object on the one hand and of the examination zone on the other hand being different, notably for detecting land mines buried in the soil, the examination zone being irradiated by gamma radiation and the annihilation radiation thus generated being measured and evaluated; the invention also relates to a device for carrying out the method.

EP-B 0 358 237 already describes a method enabling detection of inter alia explosives buried in the soil. Therein the examination zone (the soil) is irradiated by gamma radiation in a range of from 10.6 MeV to 13.0 MeV. This energy suffices to turn the nitrogen present in the explosive substances of the land mine into a radioactive isotope, but not the other substances normally present in the soil. The nitrogen isotopes decay, thus producing positrons which interact with free electrons and hence generate annihilation radiation of 0.511 MeV. The nitrogen concentration in the soil can thus be determined by measurement of the annihilation radiation. An increased concentration of nitrogen is an indication of the presence of explosives in the soil.

The gamma radiation is generated by a gamma radiation source emitting bremsstrahlung (for example, an accelerator), which source emits the gamma radiation conventionally in a pulsed manner. During the pulse intervals practically exclusively annihilation radiation is produced in the soil, so that this radiation can be readily detected so that an explosive can be detected also if it fills only a small part of the irradiated examination zone. It is a drawback of the known method that it requires a gamma radiation source supplying quantum energies of more than 10 MeV. At such energies it is difficult to achieve effective protective shielding of the operator. Moreover, irradiation makes the examination zone radioactive at least if it contains nitrogen.

It is an object of the present invention to conceive a method of the kind set forth in such a manner that detection is possible while using gamma radiation of lower energy, even if objects are situated at different depths in the examination zone.

This object is achieved according to the invention in that
a) the energy of the gamma radiation is less than 10 MeV,
b) a gamma radiation beam traversing the examination zone is formed,
c) at least the annihilation radiation generated in the examination zone is measured by a plurality of detector elements which are arranged in such a manner that they can always detect only the radiation from a respective segment of the gamma radiation beam.

The invention utilizes gamma radiation of an energy of less than 10 MeV. Consequently, the irradiated examination zone cannot become radioactive. The irradiation, however, produces electron-positron pairs which recombine, emitting annihilation radiation, after a distance of approximately 5 mm in the examination zone. The intensity of the annihilation radiation depends quadratically on the mean atomic number so that the intensity of the annihilation radiation arising in the object is higher or lower than that of the X-rays generated in the remainder of the examination zone, depending on whether the mean atomic number of the object is higher or lower. For the measurement of the radiation generated in response to the irradiation there is provided a plurality of detector elements which can "see" different segments of the gamma radiation beam. If the gamma radiation beam strikes an (explosive) object in the examination zone, the radiation measured by at least one of the detector elements will be completely dependent on the composition of this object, whereas the signals measured by the other detector elements are independent therefrom. The method according to the invention thus enables the detection of objects at a depth in the examination zone (for example, 50 cm) which is large in comparison with the dimensions of the object (for example, 5 or 10 cm).

It is to be noted that DE 30 47 824 discloses a method for the quantitative determination of the ash content of carbon which also utilizes the direct generation of electron-positron pairs. The carbon sample is then struck by the radiation of a radionuclide and the measurement of the annihilation radiation thus produced is combined with a measurement of the Compton scattered radiation. An energy-resolving detector is used for this purpose.

The irradiation of the examination zone causes, not only annihilation radiation therein but also Compton scattered radiation. If only the radiation emanating backwards is detected, i.e. backwards, in relation to the direction of the gamma radiation beam (which is inevitably so in the case of detection of an object in the soil), the energy of the Compton scattered radiation will be less than the energy of the annihilation radiation. Therefore, in a preferred version of the invention the direction of travel of the gamma quanta detected by the detector elements encloses an angle of between 90° and 180°, preferably between 120° and 160°, with respect to the direction of travel of the gamma quanta entering the examination zone. In the case of a scatter angle of 120° or more, the maximum energy of the Compton scattered radiation is less than 320 keV (in comparison with 511 keV for the annihilation radiation).

In a further version of the invention, the gamma radiation is generated by a gamma radiation source emitting a bremsstrahlung spectrum. This source may be a linear accelerator or a betatron, being capable of generating gamma radiation of an intensity which is substantially higher than that emitted by a radionuclide, even though they emit the gamma radiation in a pulsed manner only.

If the radiation from the examination zone is measured in an energy-resolving manner, only comparatively low count rates are possible, notably if the gamma radiation is emitted only in a pulsed manner. However, if measurement is not carried out in an energy-resolving manner, substantially higher count rates are possible so that a gamma radiation source of higher intensity can also be used. In order to enable measurement of the annihilation radiation again in a manner which is substantially independent of the Compton scattered radiation, a further version of the invention utilizes a filter of a material having a high atomic number for the measurement of the radiation emanating from the examination zone, which filter is proportioned so that its attenuation of the annihilation radiation is low and its attenuation of the Compton scattered radiation is considerable. For example, a uranium filter of a thickness of 2 mm has a transmission of less than 5% at 255 keV, but a transmission of 50% at 511 keV.

In a further version of the invention, one measurement is performed with filter and a second measurement is performed without filter, the measuring signals thus acquired being evaluated. When the signals obtained during the two measurements are suitably combined, the annihilation radiation and the Compton scattered radiation can be separated from one another.

A device for carrying out the method of the invention is characterized in that it includes:

a gamma radiation source emitting bremsstrahlung with a maximum energy of 10 MeV, a diaphragm device for forming a gamma radiation beam, a detector device which is connected to the gamma radiation source and includes a plurality of detector elements which are offset in the direction perpendicular to the examination zone, a slit-shaped aperture via which the individual detector element detects the annihilation radiation generated in a segment of the gamma radiation beam.

The sole view shows a device according to the invention.

The invention will be described in detail hereinafter with reference to a drawing which diagrammatically shows a device for the detection of explosive devices buried in the soil 2. Such an explosive device, in the form of a land mine, is denoted by the reference numeral 1 in the drawing. The device includes a gamma radiation source 3 which is capable of generating bremsstrahlung with a maximum energy of 5 MeV. This source may be a linear accelerator or a betatron emitting the gamma radiation in a pulsed manner. The target wherefrom the gamma radiation emanates should be situated at a distance of approximately 2 m from the ground when a reciprocating gamma radiation beam is to be generated.

A diaphragm device 4 forms a gamma radiation beam, only the central ray 5 of which is shown in the drawing. If the cross-section of the gamma radiation beam is too large, so that a substantial volume of the examination zone around the explosive device is also irradiated, intensity differences of the gamma radiation will hardly be noticeable, whereas the intensity of the annihilation radiation generated will be too low if the cross-section of the gamma radiation beam is very small. Therefore, in the examination zone the gamma radiation beam should have a cross-section which is comparable to the dimensions of the explosive device, for example approximately 5 cm. On the one hand this suffices to generate radiation of adequate intensity while on the other hand this cross-section is sufficiently small to ensure that upon detection of a land mine signals are obtained which are determined essentially by the composition of the land mine. The central ray penetrates the soil at an angle of approximately 20° with respect to the vertical.

The gamma radiation is then attenuated by two effects, i.e. by the Compton scattering and by the generation of electron-positron pairs. The Compton scattering processes change the energy of the gamma quanta in conformity with the angle enclosed by the scattered quanta with respect to the direction of the gamma quantum generating the scattered quanta. If this scatter angle is small, the energy of the gamma quanta decreases only slightly. In the case of a scatter angle of 180°, however, the gamma quanta generated by the scattering process have only an energy of less than 255 keV. The gamma quanta in the primary gamma radiation beam which have an energy of more than 1.022 MeV, i.e. more than twice the annihilation radiation, are also capable of generating electron-positron pairs which take up the excess energy of the generating gamma quantum and which recombine after an average travel of approximately 5 mm. Recombination of a positron with an electron produces two gamma quanta having an energy of 511 keV each; because the positron is annihilated by this recombination, this radiation is called annihilation radiation.

The probability of a positron-electron pair being generated is dependent on the square of the mean atomic number. Because land mines are usually filled with a plastic explosive which is rich in nitrogen, they have a lower mean atomic number than the surrounding soil ($SiO_2$). Therefore, if the gamma radiation beam strikes a land mine, the intensity of the annihilation radiation emanating therefrom will be lower than that of the annihilation radiation generated in the soil. This effect can be used to detect subterranean land mines in suspect areas.

The radiation generated in the soil is measured by a detector device 6 which is connected to the gamma radiation source 3 and includes a plurality of detector elements 61, 62, 6i which can detect, via a slit 7 extending perpendicularly to the plane of drawing, only the radiation generated in the soil within a given segment of the gamma radiation beam 5. The detector element 61 thus detects the radiation generated in the upper region of the soil, whereas the detector element 6n detects the radiation from the deepest level at which land mines are to be detected, for example the level at a depth of 50 cm. The radiation from this level preferably travels to the detector element 6n perpendicularly, because in that case it is least attenuated by the soil. The detector elements 61 . . . 6i, 6n are arranged in such a manner that the gamma quanta detected thereby follow a path to the detector element which encloses an angle of between approximately 120° and 160° with respect to the direction of the gamma radiation beam 5. Consequently, the Compton scattered radiation also reaching the detector element has a maximum energy of less than 320 keV, so that it is attenuated substantially more than the 511 keV annihilation radiation during its travel through the soil.

For additional attenuation a filter 8 of a material having a high atomic number can be arranged in the beam path of the radiation to be measured, for example in front of or behind the slit-shaped aperture 7, so that the attenuation caused by the photo effect is particularly high. A suitable filter material is, for example uranium of a thickness of 2 mm which has a transmission of less than 5% for radiation of an energy of 255 keV, but a transmission of more than 50% for radiation of 511 keV (annihilation radiation). The Compton scattered radiation can be suppressed to a high degree by means of such a filter.

However, it is also possible to perform two measurements, i.e. one measurement with a filter and one measurement without a filter. This detector element then supplies two signals $S_1$ and $S_2$ wherefrom the individual radiation components can be separately extracted by suitable linear combination. The difference measurement aims to measure the intensity of the annihilation radiation without falsification by Compton scattered radiation. The signals $S_1$ (with filter) and $S_2$ satisfy the following conditions:

$$S_1 = c(aI_c + bI_a) \quad (1)$$

$$S_2 = c(I_c + I_a) \quad (2)$$

Therein, c is a proportionality factor and a and b are the attenuation coefficients of the filter for the Compton radiation $I_c$ and the annihilation radiation $I_a$, respectively, a being small in comparison with b. The values a and b can be determined for each detector element by calibration measurements performed on known objects. The values of the signals $S_1$ and $S_2$ (measured for each detector element) are then entered in the equations (1) and (2) in order to determine the intensity $I_a$ of the annihilation radiation.

The detector elements may be strips of a suitable scintillator material which extend perpendicularly to the plane of drawing and have a cross-section of, for example 5×5 cm. These detector elements are connected so that the detector output signal is a measure of the number of gamma quanta measured per unit of time (but not of the energy of individual gamma quanta). Detector elements suitable for this purpose may have properties similar to those of detectors used for Positron Emission Tomography (PET).

In order to enable inspection of a larger volume of the soil, it is advantageous to deflect the gamma radiation beam perpendicularly to the plane of drawing (and hence parallel to the slit-shaped aperture 7). This can be achieved by means of a diaphragm device comprising an aperture which is moved in this direction, for example a kind of Nipkow disc. However, it must then be borne in mind that in the case of a bremsstrahlung of 5 MeV, the high photon energies are restricted to a cone having a half angle of aperture of approximately 10°, so that the target of the gamma radiation source 3 must be situated approximately 2.5 m above the ground if the reciprocating gamma beam is to cover a stroke of ground having a width of approximately 1 m. After inspection of each time one stroke, the whole apparatus can be displaced in the horizontal direction by means of a carriage (not shown). The displacement may be continuous at a speed which is dependent on the deflection speed of the scanning radiation beam.

I claim:

1. A method of detecting of an object in an examination zone, the mean atomic numbers of the object on the one hand and of the examination zone on the other hand being different, the method comprising irradiating the examination zone with gamma radiation;

generating annihilation radiation in response to the gamma radiation; and measuring and evaluating the annihilation radiation, wherein a) the energy of the gamma radiation is less than 10 MeV, b) a gamma radiation beam traversing the examination zone is formed, c) at least the annihilation radiation generated in the examination zone is measured by a plurality of detector elements which are arranged in such a manner that they can always detect only the radiation from a respective segment of the gamma radiation beam.

2. A method as claimed in claim 1, wherein the direction of travel of the annihilation radiation detected by the detector elements encloses an angle of between 90° and 180° about the direction of travel of the gamma radiation entering the examination zone.

3. The method of claim 2 wherein the angle is between 120° and 160°.

4. A method as claimed in claim 1, characterized in that the gamma radiation is generated by a gamma radiation source emitting a bremsstrahlung spectrum.

5. A method as claimed in claim 1, wherein measuring the annihilation radiation emanating from the examination zone comprises utilizing a filter of a material having a high atomic number, which filter is proportioned so that its attenuation of the annihilation radiation is low and its attenuation of the Compton scattered radiation is considerable.

6. A method as claimed in claim 5, wherein measuring comprises performing a first measurement with the filter and performing a second measurement without the filter, and evaluating comprises evaluating signals acquired from the first and second measurements.

7. A device for carrying out the method claimed in claim 1, characterized in that it includes:

a gamma radiation source emitting bremsstrahlung with a maximum energy of 10 MeV, a diaphragm device for forming a gamma radiation beam, a detector device which is connected to the gamma radiation source and includes a plurality of detector elements which are offset in the direction perpendicular to the examination zone, a slit-shaped aperture via which the individual detector element detects the annihilation radiation generated in a segment of the gamma radiation beam.

8. The method of claim 7 comprising detecting land mines buried in soil in response to evaluating the annihilation radiation to determine a region of lower atomic numbers.

9. The method of claim 7 wherein the gamma radiation is no more than 5 MeV.

10. The method of claim 1 wherein the energy of the gamma radiation is sufficiently less than 10 MeV to produce predominantly annihilation radiation in the respective segment.

11. The method of claim 1 wherein the detector elements are made of scintillator material.

12. The method of claim 1 wherein the energy of the gamma radiation has a value more than 1.022 MeV.

* * * * *